United States Patent [19]

Sogi et al.

[11] 4,339,537

[45] Jul. 13, 1982

[54] METHOD OF CULTURING BIOLOGICAL SUBSTANCES

[75] Inventors: Shinroku Sogi; Masao Izawa, both of Hachioji; Shinichiro Hattori, Tokyo; Ikuo Tawara, Hachioji; Daizo Shinohara, Hachioji; Sachiko Tachikawa, Hachioji, all of Japan

[73] Assignee: Olympus Optical Company Limited, Tokyo, Japan

[21] Appl. No.: 91,767

[22] Filed: Nov. 6, 1979

[30] Foreign Application Priority Data

Nov. 10, 1978 [JP] Japan .................................. 53/137786

[51] Int. Cl.³ .......................... C12N 5/00; C12M 3/04
[52] U.S. Cl. .................................... 435/240; 435/241; 435/285; 435/286
[58] Field of Search ............... 435/240, 241, 284, 285, 435/286, 29

[56] References Cited

U.S. PATENT DOCUMENTS

| | | | |
|---|---|---|---|
| 3,407,120 | 10/1968 | Weiss et al. | 435/285 X |
| 3,732,149 | 5/1973 | Santero | 435/285 |
| 3,827,943 | 8/1974 | Mann | 435/285 |
| 3,839,155 | 10/1974 | McAleer et al. | 435/285 |
| 3,925,165 | 12/1975 | Müller | 435/285 |
| 3,933,585 | 1/1976 | McAleer et al. | 435/285 X |
| 3,941,661 | 3/1976 | Noteboom | 435/285 |
| 4,224,413 | 9/1980 | Burbidge | 435/285 X |
| 4,228,243 | 10/1980 | Iizuka | 435/285 |

Primary Examiner—David M. Naff
Attorney, Agent, or Firm—Stevens, Davis, Miller & Mosher

[57] ABSTRACT

Biological substances such as tissues, cells, vaccines and viruses are cultured by the steps of: introducing a culture solution having the substances suspended therein into a closed culture vessel having a plurality of disclike implantation plates arranged horizontally with a certain space between successive plates so that a predetermined number of the implantation plates is immersed in the culture solution; culturing the substances on the surface of the implantation plates; removing the substances from the implantation plates; suspending the removed cultured substances in a new culture solution; and successively repeating the steps of culturing, removing the cultured substances and suspending in a new culture solution while each time increasing the amount of newly supplied culture solution to progressively increase the number of implantation plates immersed in the culture solution. This process enables production of a large amount of biological substance from a small amount of seed substance by mass production in a simple operation without any contamination.

5 Claims, 7 Drawing Figures

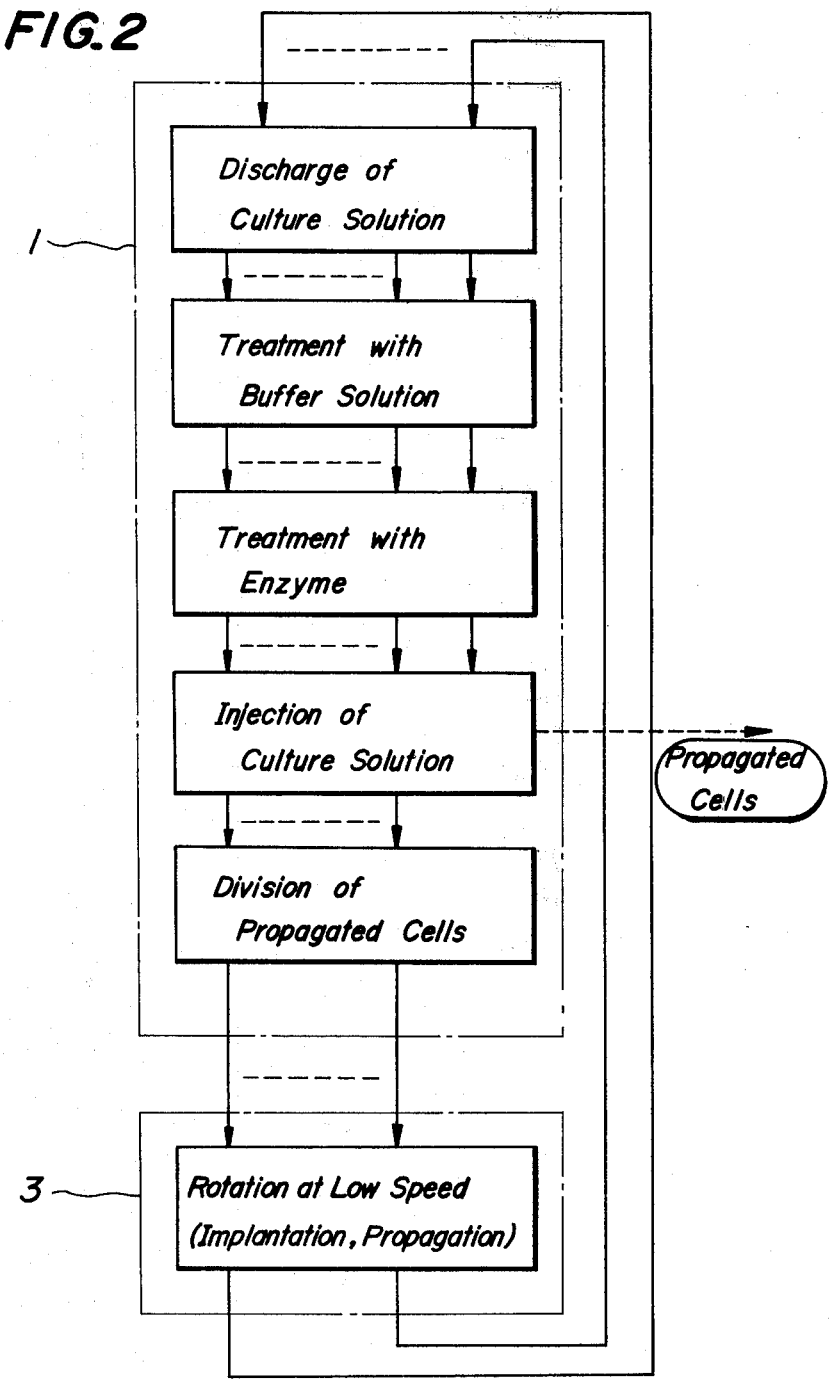

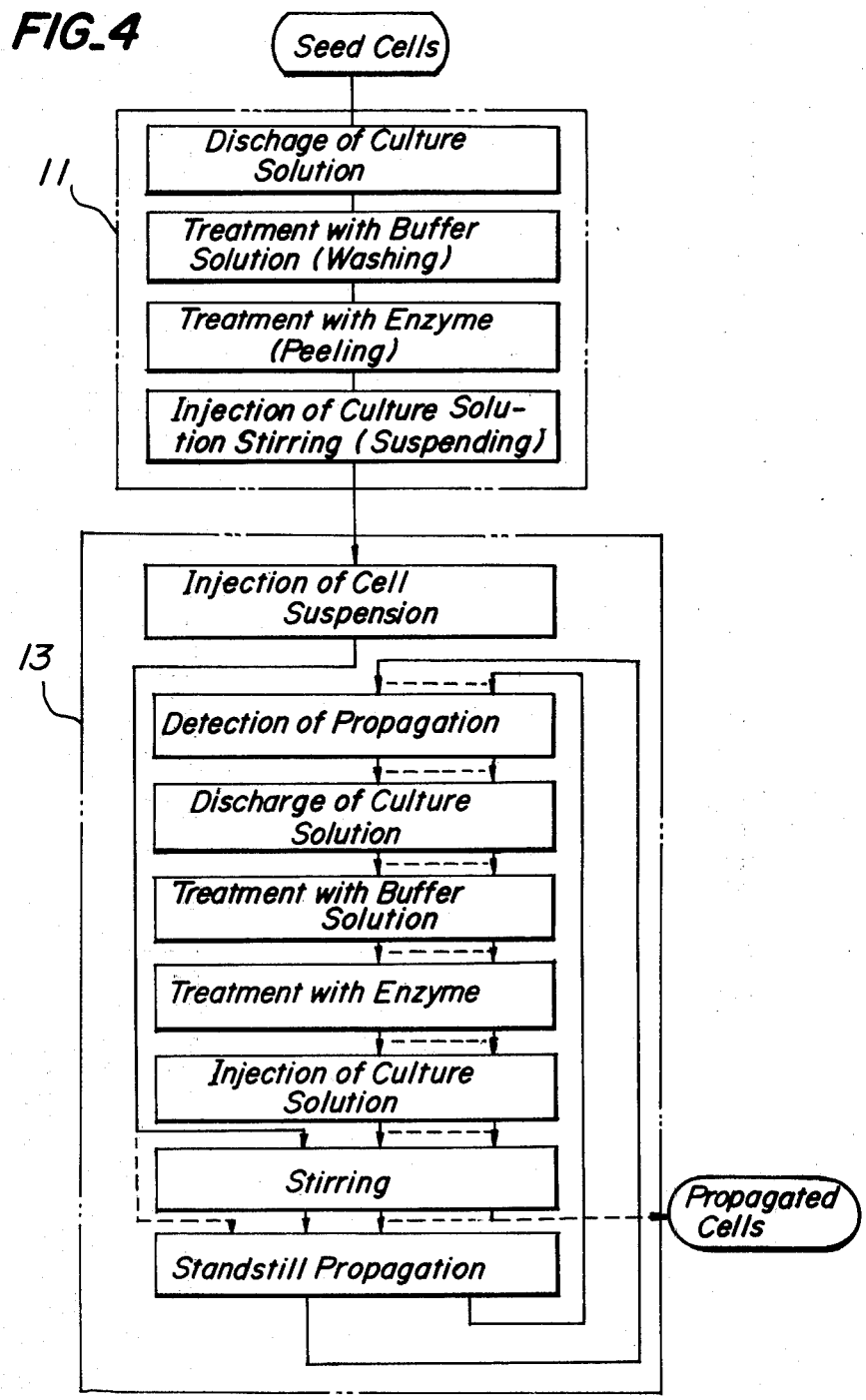

METHOD OF CULTURING BIOLOGICAL SUBSTANCES

BACKGROUND OF THE INVENTION

The present invention relates to production of biological substances such as tissues, cells, vaccines, viruses and the like.

Hitherto, various culturing apparatuses have been proposed with the development of gas culture technique for an incubator, that is, culture technique in a special gas atmosphere. For instance, as described in Japanese Patent Laid-open Publication No. 41,489/76, there is disclosed an implantation propagation method in which a gas-permeable and liquid-impermeable Teflon tube is arranged in an incubator maintained with a special gas atmosphere, seed cells to be cultured are adhered onto the inner surface of the Teflon tube and a culture solution is flowed through the tube. In U.S. patent application Ser. No. 275,642 filed on Jul. 27, 1972, now U.S. Pat. No. 3,839,155, there is described another implantation propagation method employing a propagation apparatus provided with a number of discs arranged perpendicularly and separated from each other in the horizontal direction. A small amount of a culture solution is filled in said propagation apparatus so as to immerse a part of said discs, cells to be propagated are adhered to said plurality of discs, respectively, and the cells are plated and grown by rotating said plurality of discs at a given speed.

In both of the above culturing apparatuses, however, tissues or cells are propagated on the whole surface of an implantation surface by a one-generation culture, and the whole surface area of the implantation surface is large, so that a comparatively large amount of cells are required initially, but such a large amount of cells should be prepared by previous culture and such preparation is considerably troublesome. Furthermore, an apparatus for carrying out the above method is complicated in construction, large in size, and troublesome to control. In addition, it is difficult to sterilize the portion where the cells are implanted.

As another conventional culture method, a roller bottle culture method as shown in FIG. 1 has been proposed. A schematic diagram shown in FIG. 1 will be explained with reference to a block diagram of the culture operation shown in FIG. 2. In the first place, seed cells and a given amount of a culture solution are poured in several culture bottles 2a, 2b, . . . within a clean bench 1 and the bottles are sealed by suitable plugs. Then, these culture bottles 2a, 2b, . . . are transferred to an incubator 3 maintained with a special gas atmosphere and the plugs are removed. Each bottle is placed on a pair of rotating rollers 4a, 4b, . . . and is rotated at a given speed to rotate the cells housed in the culture bottles 2a, 2b, . . . are rotated and stirred with the culture solution and implanted and propagated on the inner walls of the culture bottles 2a, 2b, . . . After completing predetermined propagation in the incubator 3, the culture bottles 2a, 2b, . . . are again transferred into the clean bench 1 after sealing the bottles with plugs, where the propagated cells are reimplanted in new culture bottles.

In order to reimplant the propagated cells in new culture bottles, it is firstly necessary to throw away the culture solution in the culture bottles 2a, 2b, . . . which completed the predetermined propagation, and the cells implanted and propagated on the inner wall of the culture bottle are washed by injecting a buffer solution. Then, the buffer solution is thrown away, an enzyme solution such as trypsin or the like is injected and the implanted and propagated cells are made to be easily peeled off the bottle wall. After that, the enzyme solution is thrown away and a new culture solution is injected. Then, the solution is repeatedly sucked and discharged by means of a pipette so that the propagated cells are peeled off the bottle wall and separated into individual cells which are stirred and suspended in the culture solution, and the cell-suspending solution is further divided into one or more new culture bottles.

In the culture method shown in FIG. 1, the desired amount of cells are obtained by repeating reimplantation and roll culture as described above, but in order to reimplant cells, it is necessary to replace the cell-suspending solution into a culture bottle of larger capacity than the culture bottle which just completed propagation or a plurality of culture bottles of equal capacity to the former culture bottle are prepared and the cell-suspending solution is separately injected into these bottles in a fixed quantity. In such method, therefore, the culture operation is troublesome, and there is the possibility of contaminating the cells at the time of reimplantation. Further, it is necessary to circulate cells to be propagated between the clean bench 1 and the incubator 3, so that the apparatus disadvantageously becomes large.

SUMMARY OF THE INVENTION

An object of the invention is to eliminate the above-described various disadvantages of conventional methods and to propose a method of growing a large amount of biological tissues and cells from a small amount of seed tissues and cells in a mass production manner by a simple operation without any contamination.

According to the invention, a method for culturing biological substances such as tissues, cells, vaccines, viruses and the like in a substantially closed culture vessel having an implantation surface comprising the steps of: (a) introducing a given small amount of biological substances together with a given amount of a culture solution into the culture vessel to such a level that a predetermined part of the implantation surface is immersed in the culture solution having the biological substances suspended therein; (b) propagating the biological substances on the immersed part of the implantation surface, while the atmosphere inside the culture vessel is controlled in a desired manner; (c) introducing into the culture vessel an agent which makes it easy to peel the propagated biological substances from the immersed part of the implantation surface and then discharging the agent; and (d) introducing a culture solution into the culture vessel to suspend uniformly the peeled biological substances therein; whereby said steps (b), (c) and (d) are successively repeated while the amount of culture solution to be introduced into the culture vessel is progressively increased in accordance with the degree of propagation of the biological substances and the area of the part of the implantation surface to be immersed in the suspension is progressively increased.

Another object of the invention is to propose an apparatus for culturing biological substances with a small and simple structure in proper arrangement for efficiently propagating the biological tissue or cell by simple control and operation.

According to the invention, an apparatus for culturing biological substances such as tissues, cells, vaccines, viruses and the like comprises: a culture vessel for defining a substantially closed culturing space; a shaft arranged in the culture vessel rotatably about a substantially vertical axis; a plurality of disc-like implantation plates secured to said shaft in such a manner that they are almost horizontally arranged and are separated from each other in the vertical direction; outlet means provided at a lower portion of the culture vessel; inlet means provided at an upper portion of the culture vessel; liquid transfer means for selectively introducing and discharging a liquid into and out of the culture vessel through said inlet means and outlet means, respectively; and means for rotating selectively said shaft and the implantation plates about said vertical axis.

BRIEF DESCRIPTION OF THE DRAWINGS

FIG. 2 is a block diagram illustrating successive steps of the culture method of FIG. 1;

FIG. 4 is a block diagram depicting successive steps of the culture method according to the invention;

DESCRIPTION OF THE PREFERRED EMBODIMENTS

The invention will be explained in detail with reference to the accompanying drawings.

Figure 1:
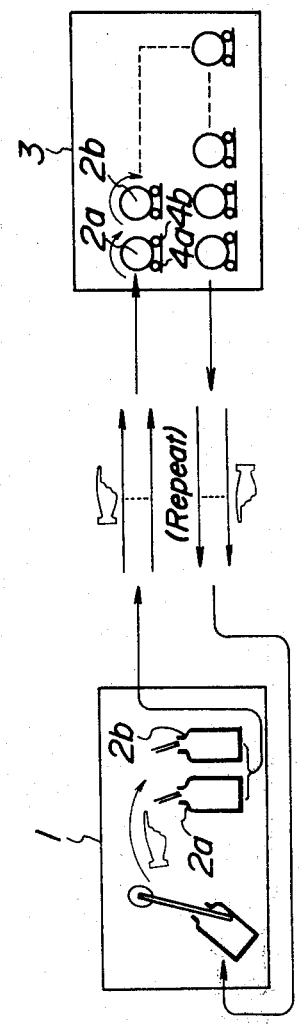
FIG. 1 is a schematic diagram showing a conventional culture method.
Figure 3:
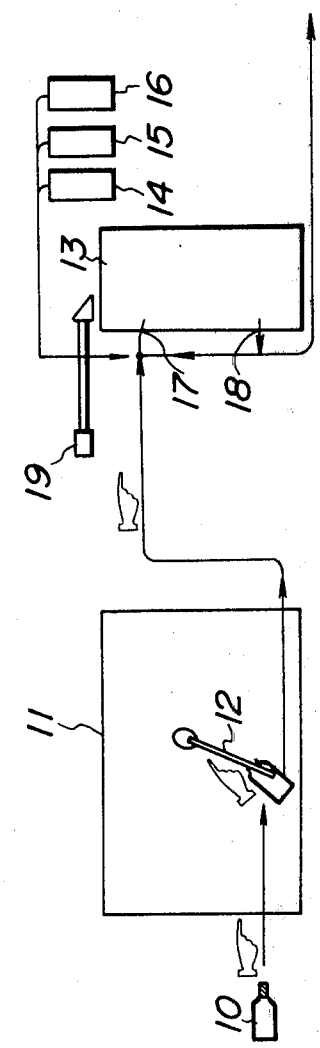
FIG. 3 is a schematic diagram showing one exemplary culture method according to the invention.

FIG. 3 is a schematic diagram showing one embodiment of the culturing method according to the invention, and FIG. 4 is a block diagram illustrating successive steps thereof. The biological tissues or cells (hereinafter referred to as "cell") to be cultured have been stored in a culture vessel 10 together with a culture solution. In the present embodiment, the culture bottle 10 is first opened within a clean bench 11, and after disposing of the old culture solution in the culture bottle 10, the inside of the bottle is rinsed with a buffer solution. Thereafter, an enzyme treatment is carried out with the use of trypsin so as to make it easy to peel the cells implanted on the inner wall of the culture bottle 10 therefrom. Then, after disposing of the trypsin, a new culture solution of almost the same amount as that of the disposed culture solution is injected into the bottle, stirred with a pipette 12, and the cells are peeled, separated and suspended in the culture solution. Thereafter, the cell-suspending solution is divided into several other culture bottles by a given amount, a new culture solution is further injected into one of these culture bottles, and the solution is diluted to a predetermined cell concentration. Next, the cell-suspending solution (sample solution) diluted by the predetermined cell concentration is transferred into a culture vessel 13.

The culture vessel 13 has a predetermined implantation surface, whose inside is kept at a special gas atmosphere, and in the present embodiment, $CO_2$:5%, air:95%, humidity:100% and temperature:37° C. Further, the culture vessel 13 is provided with an inlet 17 for selectively injecting or delivering said sample solution, culture solution 14, buffer solution 15 and enzyme solution 16, and an outlet 18 for selectively disposing of these solutions.

At first, an amount of said sample solution is injected from the inlet 17 in the culture vessel 13 by such an amount that a part of the implantation surface is immersed, and after stirring or immediately after injection, standstill cultivation is started. The implantation and propagation condition of cells at a part of the implantation surface in the culture vessel 13 is detected by a propagation detecting device 19 such as a microscope and the like. After confirming with the detecting device 19 that the predetermined propagation on the implantation surface has been completed, the used culture solution in the culture vessel 13 is disposed of from the outlet 18. Thereafter, the buffer solution 15 is injected so as to rinse the cells propagated on the implantation surface and then disposed of. After that, the enzyme solution 16 is injected to make it easy to peel the implanted cells from the implantation surface. Next, the enzyme solution is disposed of, and a new culture solution 14 is injected. Then, the cells are peeled from the surface and separated into individual cells which are then suspended in the culture solution. In this case, the cells and the culture solution may be stirred by, for instance, rotating or vibrating the implantation surface in the culture vessel 13. Further, the amount of the culture solution 14 newly injected is so determined that the cell concentration is almost equal to that of the original seed cell solution. Such a cell concentration may be achieved before or during or after stirring.

After that, the propagated cells are again subjected to the steps of the above-described standstill cultivation→propagation detection→culture solution disposal→buffer solution treatment→enzyme treatment→culture solution injection→stirring in the same culture vessel 13 in succession, and as a result, the originally injected cells are successively cultured and a large amount of propagated cells can be obtained.

In the method according to the invention, a desired amount of successive cultivation can be made in a single culture vessel without carrying out any artificial reimplantation operation, and as a result, a small amount of cells is sufficient enough as seed cells and there is no possibility of contamination. In addition, since various treatments are carried out in the same culture vessel, homogeneously propagated cells can be obtained and the operation is comparatively simple.

In addition, in the method according to the invention, it is preferable to culture cells to be propagated by slightly moving on the implantation surface in the culture vessel. In addition, after diluting the propagated cells into a predetermined concentration with the use of a culture solution, it is preferable to circulate the cell-suspending solution through the outlet 18 and the inlet 17. In this manner, the propagated cells and the culture solution are more positively and uniformly stirred, so that a cell-suspending solution having a uniform pH value can be obtained and thus homogeneously propagated cells can be obtained. Moreover, in the method according to the invention, at the time when cells have been propagated on the whole implantation surface or at the time when cells have been propagated to a desired amount, successive cultivation is stopped, and the cells at this time may be taken out of the outlet 18 according to treating steps similar to the above steps.

Figure 5:
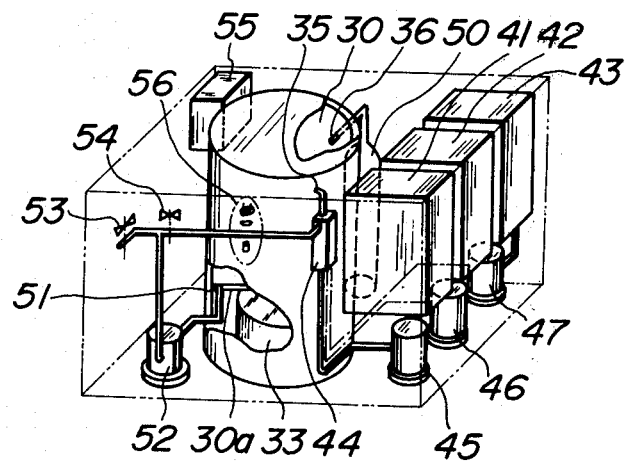
FIG. 5 is a perspective view of external appearance of one embodiment of a culture apparatus according to the invention, partly broken away.
Figure 6:
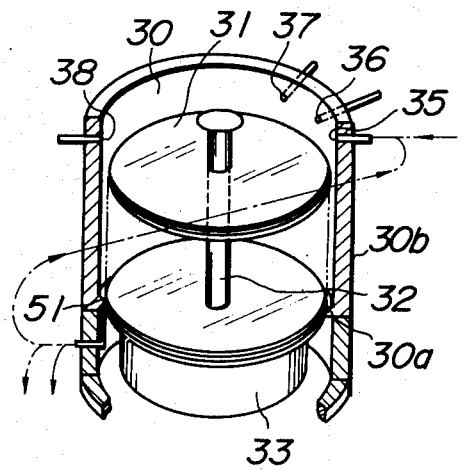
FIGS. 6 and 7 are a cross-sectional perspective view and a cross-sectional view, respectively, showing an embodiment of a culture vessel used for the apparatus shown in FIG. 5.
Figure 7:
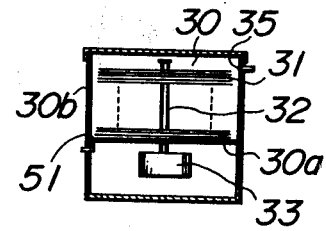

FIG. 5 is a perspective view of the external appearance of one embodiment of the essential portion of a culturing apparatus according to the invention, partly broken, and FIGS. 6 and 7 are a cross-sectional perspective view and a cross-sectional view, respectively, showing one embodiment of a culture vessel used for the apparatus shown in FIG. 5. A culture vessel 30 comprises a plurality (64 in the present embodiment) of rotatable disc-like implantation plates 31 separated from each other through spacers (not shown) in the vertical direction and arranged in the horizontal direction. These implantation plates are detachably coupled to a drive shaft 32 and integrally rotated by a drive motor 33. At the upper portion of the culture vessel 30 are provided a liquid supply inlet 35, an atmosphere control valve 36, a degassing outlet 37 and a sterilizer 38. The liquid supply inlet 35 selectively injects a sample solution prepared by diluting initial cells to be cultured to a predetermined concentration with a culture solution and chemical solutions filled in a culture solution tank 41, a buffer solution tank 42 and an enzyme solution tank 43, respectively, into the culture vessel 30. The sample solution is injected through a self-seal mechanism (for example, a rubber stopper or the like) (not shown) and a preheater 44, while the chemical solutions filled in each tank 41, 42, 43 are injected through a valve (not shown), a filter and said preheater 44. The atmosphere control valve 36 is coupled to a $CO_2$ gas cylinder 50 through a filter (not shown) and a valve and injects $CO_2$ and air by properly mixing with each other ($CO_2$:5%, air:95%) for the purpose of maintaining a constant pH of the culture solution injected in the culture vessel 30. The degassing outlet 37 discharges the residual gas after sterilization or the supplied air during culture through a valve (not shown) and a filter. The sterilizer 38 is coupled to a sterilizing device such as an ethylene oxide gas generator or the like through a filter (not shown) and a valve and sterilizes the portion where cells in the culture vessel 30 or the like before starting the culture operation.

On the other hand, a bottom plate 30a of the culture vessel 30 is provided with a liquid outlet 51 which selectively discharges or recovers the solution injected into the culture vessel 30 in the process of culture through a pump 52 and a valve 53 and circulates the cell-suspension after predetermined propagation in the culture vessel 30 through the pump 52, a valve 54, the preheater 44 and the liquid supply inlet 35.

The above-described culture vessel 30 comprises a heater (not shown) provided in a side wall 30b thereof for maintaining the inside of the vessel at a predetermined temperature (37° C.) under control of a temperature controller 55. Further, in a liquid path between the pump 52 and the liquid supply inlet 35 is provided an observation portion 56 for detecting a culture density of the cell suspension after predetermined propagation in a photoelectric manner or image information processing manner. Further, there is not illustrated but in the culture apparatus of the present embodiment, on the implantation plate 31 in the culture vessel 30 are provided a propagation detection device for observing the propagation state of cells and a detection device for controlling the gas atmosphere and the temperature in the culture vessel 30 and the pH of the culture solution, together with a control device such as a minicomputer or the like for controlling the culture steps by driving the various valves based on information from these detection devices and said observation portion 56. In addition, said propagation detection device can be constructed by detachably providing an objective lens of, for instance a vertical-type microscope, in the culture vessel 30.

One example of culturing stops of cells by means of culture devices shown in FIGS. 5-7 will be explained in order.

(i) All the valves except that for the sterilizer are closed and said sterilizer is actuated to sterilize the inside of the culture vessel.

(ii) After sterilization for a suitable time, the residual air is discharged from the degassing outlet 37 (in case of sterilizing with ethylene oxide gas).

(iii) An initial sample solution containing a small amount of seed cells is injected in the culture vessel 30 from the liquid supply inlet 35.

(iv) A culture solution sufficient to propagate the cells in the injected sample solution to a number of cells having a predetermined propagation magnification (which will be explained as 4 times hereinafter) is injected from the culture solution vessel 41 through the pump 45, the valve, the filter, the preheater 44 and the liquid supply inlet 35. In addition, in the present embodiment, the culture solution in this case is sufficient to immerse the lowermost implantation plate 31 in the culture solution, and an amount of seed cells is sufficient to cover approximately ¼ of the upper surface area of said implantation plate 31. In this case, therefore, the culture is completed when the cells form a closely packed single layer on the upper surface of the lowermost implantation plate 31. It should be noted that the cells are easily implanted on the upper surface of the plate 31 which is made of material such as titanium, teflon, hard glass, but are plated with difficulty on the lower surface of plate 31 and the bottom 30a of the culture vessel 30 which is made of material such as stainless steel on which the cells are implanted with difficulty. Therefore, the amount of cells grown on the lower surface of plate 31 and the bottom surface 30a may be neglected.

(v) The motor 33 is driven for rotating the implantation plate 31 and uniformly distributing the cells in the culture solution.

(vi) The standstill culture is carried out by properly maintaining the gas atmosphere, temperature, humidity in the culture vessel 30 and the pH in the culture solution, and waiting for implantation and propagation of the cells all over the upper surface of the lowermost implantation plate 31.

(vii) The propagation of the cells all over the implantation plate by means of the propagation detection device is detected.

(viii) The old culture solution is discharged through the waste liquid outlet 51, the pump 52 and the valve 53.

(iv) The buffer solution is injected from the buffer solution vessel 42 through the pump 46, the valve, the filter, the preheater 44 and the liquid supply inlet 35, the cells implanted and propagated are washed, and the solution is discharged through the same path as in the above (viii).

(x) The enzyme solution (for example, trypsin) is injected from the enzyme solution vessel 43 through the pump 47, the valve, the filter, the preheater 44 and the liquid supply inlet 35 to make it easy to peel the cells implanted and propagated from the implantation plate, and the solution is discharged through the same path as in the above (viii).

(xi) The culture solution is injected from the culture solution vessel 41 to the culture vessel 30 through the same path as in the above (iv), while the motor 33 is driven to rotate the implantation plate 31 at a high speed, the implanted cells are peeled from the implantation plate, stirred, separated and suspended in the culture solution. In addition, the amount of the culture solution in this case is increased 4 times the amount of the culture solution discharged at the above (viii) because the propagation magnification is increased 4 times, or 4 times the amount of the culture solution is injected and stirred, or it is preferable to stir the cells with a lesser amount of the culture solution and then a remaining amount of the culture solution is injected thereto. Then, the lowermost four implantation plates are immersed in the solution.

(xii) The cell suspension in the culture vessel 30 is circulated through the waste liquid outlet 51, the pump 52, the valve 54, the preheater 44 and the liquid supply inlet 35.

(xiii) The above steps (vi)-(xii) are successively repeated and the cells are implanted and propagated on all 64 implantation plates.

(xiv) The above steps (viii)-(xii) are successively repeated and the cell suspension, propagated to a predetermined amount (256 times the initial cell amount in the present embodiment), is recovered through the same path. In addition, the amount of the culture solution in this case corresponds to approximately 1 time the propagation magnification.

According to the above described embodiment, the cell suspension after propagation is circulated through the vessel 30, so that the stirring becomes more positive and the pH of the culture solution becomes uniform. Further, an ethylene oxide gas generator or the like is used as a sterilizer, so that it is advantageous to carry out the sterilization easily.

As stated above, with the use of the apparatus according to the invention, cells are successively propagated in one culture vessel, so that not only the successive culture can be performed, but also the apparatus can be formed into a small and simple construction. Accordingly, a large amount of cells can continuously be obtained from a small amount of cells by a single apparatus, the control becomes comparatively simple, and automation also becomes easy. Further, in the process of successive propagation, the cells are not transferred to the outside of the culture vessel, so that homogeneous cells can be obtained without any possibility of contamination.

In addition, in the apparatus according to the invention, a plurality of implantation plates can be constructed as an umbrella-shape having an inclined surface. Besides, it is preferable to culture the cells by rotating the implantation plates at a low speed. In this manner, the cells adhered to the upper surfaces of the implantation plates are always put into contact with a new culture solution by being stirred and rotated in the culture solution, and as a result, the propagation effect can be improved. Further, after the thus propagated cells are separated and suspended in a new culture solution, it is not always necessary to circulate the cell suspension. Further, the propagation magnification is not limited to 4 times but any desired magnification, such as 2 times, 8 times or the like, and the number of implantation plates can optionally be changed accordingly. Further, the cell suspension can be recovered from the vessel when the amount of propagated cells has reached any desired amount.

What is claimed is:

1. A method of culturing biological substances capable of propagation in a culture solution, said method comprising culturing the biological substances in a substantially closed culture space formed by a culture vessel containing a plurality of implantation plates which are arranged substantially horizontally and spaced from each other in a vertical direction by the steps of:
   (a) introducing a given small amount of biological substances together with a given amount of culture solution into the culture vessel to such a level that a predetermined number of the implantation plates is immersed in the culture solution having the biological substances suspended therein;
   (b) propagating the biological substances on the surface of the immersed implantation plates, while an atmosphere inside the culture vessel is controlled in a desired manner;
   (c) introducing into the culture vessel an agent which makes it easy to peel the propagated biological substances from the surface of the immersed implantation plates, peeling the biological substances from the plates and then discharging the agent;
   (d) introducing a culture solution into the culture vessel to suspend uniformly the peeled biological substances therein;
   (e) repeating said steps (b), (c) and (d) in succession, while the propagated biological substances are kept in the culture vessel and the number of implantation plates to be immersed in the culture solution having the biological substances suspended therein is progressively increased by increasing the amount of culture solution introduced into the culture vessel in step (d).

2. The method according to claim 1, further comprising between the steps (b) and (c),
   a step of discharging the culture solution when propagation is complete; and
   a step of washing the propagated substances on the surface of the implantation plates with a buffer solution.

3. The method according to claim 1, wherein the agent for making it easy to peel the propagated substances from the implantation plates is an enzyme.

4. The method according to claim 1, further comprising between the steps (c) and (d),
   a step for moving mechanically the implantation plates so as to promote the peeling of the propagated substances from the implantation plates.

5. The method according to claim 1, further comprising between the steps (b) and (c),
   a step for detecting the propagation condition of the biological substances grown on the implantation plates.

* * * * *